US010137734B2

(12) United States Patent
Gander et al.

(10) Patent No.: US 10,137,734 B2
(45) Date of Patent: *Nov. 27, 2018

(54) RUBBER COMPOSITION COMPRISING A 1,3-DIPOLAR COMPOUND ADDITIVE BEARING AN IMIDAZOLE FUNCTIONAL GROUP

(71) Applicants: COMPAGNIE GENERALE DES ETABLISSEMENTS MICHELIN, Clermont-Ferrand (FR); Michelin Recherche et Technique S.A., Granges-Paccot (CH)

(72) Inventors: Sophie Gander, Clermont-Ferrand (FR); Anne-Frédérique Salit, Clermont-Ferrand (FR); Nicolas Seeboth, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 26 days.

This patent is subject to a terminal disclaimer.

(21) Appl. No.: 15/031,407

(22) PCT Filed: Oct. 24, 2014

(86) PCT No.: PCT/EP2014/072845
§ 371 (c)(1),
(2) Date: Apr. 22, 2016

(87) PCT Pub. No.: WO2015/059274
PCT Pub. Date: Apr. 30, 2015

(65) Prior Publication Data
US 2016/0263943 A1 Sep. 15, 2016

(30) Foreign Application Priority Data
Oct. 25, 2013 (FR) .................... 13 60415

(51) Int. Cl.
| | |
|---|---|
| *B60C 1/00* | (2006.01) |
| *B60C 11/00* | (2006.01) |
| *C08K 5/3447* | (2006.01) |
| *C08K 3/36* | (2006.01) |
| *C07D 233/64* | (2006.01) |
| *C08C 19/22* | (2006.01) |
| *C08K 5/3445* | (2006.01) |
| *C08L 7/00* | (2006.01) |
| *C08L 9/06* | (2006.01) |

(52) U.S. Cl.
CPC ............ *B60C 1/0016* (2013.01); *B60C 1/00* (2013.01); *B60C 11/0008* (2013.01); *C07D 233/64* (2013.01); *C08C 19/22* (2013.01); *C08K 3/36* (2013.01); *C08K 5/3445* (2013.01); *C08K 5/3447* (2013.01); *C08L 7/00* (2013.01); *C08L 9/06* (2013.01); *B60C 2011/0025* (2013.01)

(58) Field of Classification Search
CPC .......... C08K 3/36; C08K 5/3447; B60C 1/00; B60C 11/00
USPC ...................................................... 524/575
See application file for complete search history.

(56) References Cited

U.S. PATENT DOCUMENTS

| | | | |
|---|---|---|---|
| 4,803,282 A | 2/1989 | St. Georgiev et al. ....... 548/336 |
| 5,140,055 A | 8/1992 | Hirata et al. .................... 524/93 |
| 5,185,324 A | 2/1993 | Ruger et al. .................... 514/18 |
| 5,346,962 A * | 9/1994 | Hergenrother ...... C08F 290/048 525/244 |
| 5,717,022 A * | 2/1998 | Beckmann ............ B60C 1/0016 152/450 |
| 6,034,250 A | 3/2000 | Goldstein et al. ......... 548/336.1 |
| 6,194,461 B1 | 2/2001 | Ikeda et al. .................. 514/579 |
| 6,774,255 B1 | 8/2004 | Tardivat et al. .............. 556/427 |
| 7,186,845 B2 | 3/2007 | Fukushima et al. .......... 548/257 |
| 7,199,175 B2 | 4/2007 | Vasseur .......................... 524/492 |
| 7,250,463 B2 | 7/2007 | Durel et al. ................... 524/492 |
| 7,300,970 B2 | 11/2007 | Durel et al. ................... 524/493 |
| 7,488,768 B2 | 2/2009 | Tardivat et al. .............. 524/262 |
| 7,491,767 B2 | 2/2009 | Durel et al. ................... 524/493 |
| 7,825,183 B2 | 11/2010 | Robert et al. ................. 524/476 |
| 7,834,074 B2 | 11/2010 | Brunelet et al. .............. 524/318 |
| 7,882,874 B2 | 2/2011 | Robert et al. .............. 152/209.1 |
| 7,900,667 B2 | 3/2011 | Vasseur ...................... 152/209.1 |
| 8,278,451 B2 | 10/2012 | Becker et al. ................. 546/112 |
| 8,324,310 B2 | 12/2012 | Robert et al. ................. 524/518 |
| 8,492,475 B2 | 7/2013 | Araujo Da Silva et al. ................. 524/552 |
| 9,010,393 B2 | 4/2015 | Araujo Da Silva et al. ................. 524/575.5 |
| 9,394,434 B2 | 7/2016 | Araujo da Silva et al. ................. C08L 9/06 |
| 2003/0212185 A1 | 11/2003 | Vasseur ......................... 524/492 |
| 2004/0051210 A1 | 3/2004 | Tardivat et al. .............. 264/349 |
| 2005/0004297 A1 | 1/2005 | Durel et al. ................... 524/493 |
| 2005/0016650 A1 | 1/2005 | Durel et al. ............... 152/209.1 |
| 2005/0016651 A1 | 1/2005 | Durel et al. ............... 152/209.1 |

(Continued)

FOREIGN PATENT DOCUMENTS

| | | |
|---|---|---|
| CN | 101580558 A | 11/2009 |
| CN | 102985444 A | 3/2013 |

(Continued)

OTHER PUBLICATIONS

Office Action dated Dec. 13, 2016, in counterpart CN application No. 201480058476.9 (10 pages including partial English translation).

(Continued)

*Primary Examiner* — Deve E Valdez
(74) *Attorney, Agent, or Firm* — Fitzpatrick, Cella, Harper & Scinto

(57) ABSTRACT

A rubber composition is based on at least one diene elastomer, a reinforcing filler and a 1,3-dipolar compound bearing an imidazole functional group. Such a composition exhibits an improved compromise in certain properties such as stiffness in the cured state and hysteresis.

26 Claims, No Drawings

(56) References Cited

U.S. PATENT DOCUMENTS

| | | | |
|---|---|---|---|
| 2007/0112120 A1 | 5/2007 | Vasseur | 524/492 |
| 2008/0009564 A1 | 1/2008 | Robert et al. | 523/351 |
| 2008/0156404 A1 | 7/2008 | Brunelet et al. | 152/209.1 |
| 2009/0186961 A1 | 7/2009 | Araujo Da Silva et al. | 523/150 |
| 2009/0209709 A1 | 8/2009 | Araujo Da Silva et al. | 525/333.1 |
| 2009/0234066 A1 | 9/2009 | Araujo Da Silva et al. | 524/571 |
| 2009/0286900 A1 | 11/2009 | Ichikawa et al. | 522/113 |
| 2009/0292063 A1 | 11/2009 | Robert et al. | 524/518 |
| 2010/0204359 A1 | 8/2010 | Robert et al. | 523/157 |
| 2011/0152458 A1 | 6/2011 | Araujo Da Silva et al. | 525/102 |
| 2012/0225233 A1 | 9/2012 | Guy et al. | 428/36.9 |
| 2012/0245270 A1 | 9/2012 | Blanchard et al. | 524/388 |
| 2013/0123418 A1 | 5/2013 | Araujo Da Silva et al. | 524/575 |
| 2013/0131279 A1 | 5/2013 | Araujo Da Silva et al. | 525/333.1 |
| 2013/0331475 A1 | 12/2013 | Ichikawa et al. | C08C 19/22 |
| 2015/0322234 A1 | 11/2015 | Fleury et al. | C08K 3/36 |
| 2016/0251456 A1 | 9/2016 | Ugolnikov et al. | C08F 8/30 |
| 2016/0264753 A1 | 9/2016 | Salit et al. | C08K 3/36 |

FOREIGN PATENT DOCUMENTS

| | | |
|---|---|---|
| EP | 0 257 289 A2 | 3/1988 |
| EP | 0 257 391 A2 | 3/1988 |
| EP | 0 310 061 A1 | 4/1989 |
| EP | 0 373 549 A2 | 6/1990 |
| EP | 0 945 426 A1 | 9/1999 |
| EP | 0 967 207 A1 | 12/1999 |
| FR | 2 946 050 A1 | 12/2010 |
| JP | 2012-082265 A | 4/2012 |
| JP | 2013-087182 A | 5/2013 |
| WO | 96/37547 | 11/1996 |
| WO | 99/28380 | 6/1999 |
| WO | 02/10269 A2 | 2/2002 |
| WO | 02/30939 A1 | 4/2002 |
| WO | 02/31041 A1 | 4/2002 |
| WO | 03/002648 A1 | 1/2003 |
| WO | 03/002649 A1 | 1/2003 |
| WO | 03/016387 A1 | 2/2003 |
| WO | 2005/087859 A1 | 9/2005 |
| WO | 2006/045088 A1 | 4/2006 |
| WO | 2006/061064 A1 | 6/2006 |
| WO | 2006/125532 A1 | 11/2006 |
| WO | 2006/125533 A1 | 11/2006 |
| WO | 2006/125534 A1 | 11/2006 |
| WO | 2007/017060 A1 | 2/2007 |
| WO | 2008/002614 A2 | 1/2008 |
| WO | 2011/045131 A1 | 4/2011 |
| WO | 2012/007441 A1 | 1/2012 |
| WO | WO 2012/007442 A1 | 1/2012 |

OTHER PUBLICATIONS

B. Cavalleri, et al., "Synthesis and Biological Activity of Some Vinyl-Substituted 2-Nitroimidazoles," J. Med. Chem., vol. 20, No. 5, pp. 656-660 (1977).

S. Brunauer, et al., "Adsorption of Gases in Multimolecular Layers", J. Am. Chem. Soc., vol. 60, pp. 309-319 (1938).

I.G. Zenkevich, et al., "Identification of Alyklarene Chloromethylation Products Using Gas-Chromatographic Retention Indices", Russian Journal of General Chemistry, vol. 77, No. 4, pp. 611-619 (2007)(English translation of Zhurnal Obshchei Khimii, vol. 77, No. 4, pp. 653-662(2007)).

A. P. Yakubov, et al., "Synthesis of Sterically Hindered Aromatic Aldehydes", M. M., Bulletin of the Academy of Sciences of the USSR, Division of Chemical Science, vol. 40, No. 7.2, pp. 1427-1432 (1991)(English Translation of Izvestiya Akademii Nauk SSSR, Seriya Khimicheskaya, No. 7, pp. 1609-1615 (1991)).

\* cited by examiner

RUBBER COMPOSITION COMPRISING A 1,3-DIPOLAR COMPOUND ADDITIVE BEARING AN IMIDAZOLE FUNCTIONAL GROUP

FIELD OF THE INVENTION

The field of the present invention is that of diene rubber compositions reinforced by a filler which can be used in particular in the manufacture of tyres for vehicles. It relates more particularly to the treads of tyres having a low rolling resistance.

RELATED ART

Ideally, a tread should offer a tyre a very good level of road behaviour on a motor vehicle. This level of road behaviour can be contributed by the use, in the tread, of a rubber composition carefully chosen due to its rather high stiffness in the cured state. In order to increase the stiffness in the cured state of a rubber composition, it is known, for example, to increase the content of filler or to reduce the content of plasticizer in the rubber composition or also to introduce styrene and butadiene copolymers having a high styrene content into the rubber composition. However, some of these solutions generally have the disadvantage of increasing the hysteresis of the rubber composition.

Conversely, weakly hysteretic compositions generally exhibit a low stiffness in the cured state. It may prove to be necessary to overcome this fall in stiffness in the cured state in order to provide satisfactory road behaviour. For example, the Applicant Companies have described, in Patent Application WO 2011045131, a solution which makes it possible to increase the stiffness in the cured state of a weakly hysteretic rubber composition. This solution consists in introducing glycerol into the rubber composition.

The Applicant Companies, continuing their efforts to obtain a rubber composition which is stiff in the cured state and weakly hysteretic, have discovered that the introduction of a certain 1,3-dipolar compound into a diene rubber composition reinforced by a filler makes it possible to achieve this aim.

BRIEF DESCRIPTION OF EMBODIMENTS OF THE INVENTION

A subject-matter of the present invention is a rubber composition based on at least one diene elastomer, a reinforcing filler and a 1,3-dipolar compound corresponding to the formula (I):

Q-A-B          (I)

in which:
Q comprises a dipole containing at least and preferably one nitrogen atom,
A, which is preferably divalent, is an atom or a group of atoms connecting Q to B,
B comprises an imidazole ring corresponding to the formula (II):

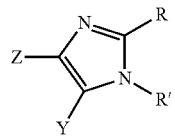

(II)

in which:
three of the four symbols Z, Y, R and R', which are identical or different, each represent an atom or a group of atoms, it being possible for Z and Y to form, together with the carbon atoms to which they are attached, a ring,
and the fourth symbol Z, Y, R or R' denotes a direct attachment to A.

Another subject-matter of the invention is a process for preparing a rubber composition based on at least one diene elastomer, a 1,3-dipolar compound corresponding to the formula (I) as defined above, a reinforcing filler and a crosslinking system, which process comprises the following stages:
adding, during a first "non-productive" stage, to the diene elastomer, the 1,3-dipolar compound, the reinforcing filler and, if appropriate, a coupling agent, by kneading thermomechanically until a maximum temperature of between 130° C. and 200° C. is reached,
cooling the combined mixture to a temperature of less than 100° C.,
subsequently incorporating the crosslinking system,
kneading everything up to a maximum temperature of less than 120° C.

Another subject-matter of the invention is a tread comprising the rubber composition in accordance with the invention.

A further subject-matter of the invention is a tyre comprising the rubber composition in accordance with the invention, in particular in its tread.

I. DETAILED DESCRIPTION OF THE INVENTION

In the present description, unless expressly indicated otherwise, all the percentages (%) shown are % by weight. The abbreviation "phr" means parts by weight per hundred parts of elastomer (of the total of the elastomers, if several elastomers are present).

Furthermore, any interval of values denoted by the expression "between a and b" represents the range of values greater than "a" and lower than "b" (that is to say, limits a and b excluded), whereas any interval of values denoted by the expression "from a to b" means the range of values extending from "a" up to "b" (that is to say, including the strict limits a and b).

The expression "composition based on" should be understood as meaning, in the present description, a composition comprising the mixture and/or the in situ reaction product of the various constituents used, some of these base constituents (for example the elastomer, the filler or other additive conventionally used in a rubber composition intended for the manufacture of tyres) being capable of reacting or intended to react with one another, at least in part, during the various phases of manufacture of the composition intended for the manufacture of tyres.

An essential characteristic of the rubber composition according to the invention is that of comprising a diene elastomer.

A "diene" elastomer (or without distinction rubber) should be understood, in a known way, as meaning an (or several) elastomer composed, at least in part (i.e., a homopolymer or a copolymer), of diene monomer units (monomers bearing two conjugated or non-conjugated carbon-carbon double bonds).

These diene elastomers can be classified into two categories: "essentially unsaturated" or "essentially saturated". Generally, "essentially unsaturated" is understood to mean a diene elastomer resulting at least in part from conjugated diene monomers having a content of units of diene origin (conjugated dienes) which is greater than 15% (mol %); thus it is that diene elastomers such as butyl rubbers or copolymers of dienes and α-olefins of EPDM type do not come within the preceding definition and can in particular be described as "essentially saturated" diene elastomers (low or very low content, always less than 15%, of units of diene origin). In the category of "essentially unsaturated" diene elastomers, "highly unsaturated" diene elastomer is understood to mean in particular a diene elastomer having a content of units of diene origin (conjugated dienes) which is greater than 50%.

Given these definitions, diene elastomer capable of being used in the compositions in accordance with the invention is understood more particularly to mean:

(a)—any homopolymer of a conjugated diene monomer, in particular any homopolymer obtained by polymerization of a conjugated diene monomer having from 4 to 12 carbon atoms;

(b)—any copolymer obtained by copolymerization of one or more conjugated dienes with one another or with one or more vinylaromatic compounds having from 8 to 20 carbon atoms;

(c)—a ternary copolymer obtained by copolymerization of ethylene and an α-olefin having from 3 to 6 carbon atoms with a non-conjugated diene monomer having from 6 to 12 carbon atoms, such as, for example, the elastomers obtained from ethylene and propylene with a non-conjugated diene monomer of the abovementioned type, such as, in particular, 1,4-hexadiene, ethylidenenorbornene or dicyclopentadiene;

(d)—a copolymer of isobutene and isoprene (butyl rubber) and also the halogenated versions, in particular chlorinated or brominated versions, of this type of copolymer.

Although it applies to any type of diene elastomer, a person skilled in the art of tyres will understand that the present invention is preferably employed with essentially unsaturated diene elastomers, in particular of the above type (a) or (b).

In the case of copolymers of the type (b), the latter comprise from 20% to 99% by weight of diene units and from 1% to 80% by weight of vinylaromatic units.

The following are suitable in particular as conjugated dienes: 1,3-butadiene, 2-methyl-1,3-butadiene, 2,3-di($C_1$-$C_5$ alkyl)-1,3-butadienes, such as, for example, 2,3-dimethyl-1,3-butadiene, 2,3-diethyl-1,3-butadiene, 2-methyl-3-ethyl-1,3-butadiene or 2-methyl-3-isopropyl-1,3-butadiene, an aryl-1,3-butadiene, 1,3-pentadiene or 2,4-hexadiene.

The following, for example, are suitable as vinylaromatic compounds: styrene, ortho-, meta- or para-methylstyrene, the "vinyltoluene" commercial mixture, para-(tert-butyl) styrene, methoxystyrenes, chlorostyrenes, vinylmesitylene, divinylbenzene or vinylnaphthalene.

Preferably, the diene elastomer is an essentially unsaturated elastomer selected from the group consisting of polybutadienes, polyisoprenes, butadiene copolymers, isoprene copolymers and the mixtures of these elastomers. Very particularly suitable as diene elastomer is a polybutadiene (BR), a copolymer of butadiene and styrene (SBR), a natural rubber (NR) or a synthetic polyisoprene (IR) preferably exhibiting a molar content of cis-1,4-bonds of greater than 90%.

The rubber composition in accordance with the invention comprises a 1,3-dipolar compound. The term "1,3-dipolar compound" is understood according to the definition given by the IUPAC.

The 1,3-dipolar compound corresponds to the formula (I):

in which:

Q comprises a dipole containing at least and preferably one nitrogen atom,

A, which is preferably divalent, is an atom or a group of atoms connecting Q to B, B comprises an imidazole ring corresponding to the formula (II):

in which:

three of the four symbols Z, Y, R and R', which are identical or different, each represent an atom or a group of atoms, it being possible for Z and Y to form, together with the carbon atoms to which they are attached, a ring (of course, when neither Z nor Y denotes the $4^{th}$ symbol), and just the fourth symbol denotes a direct attachment to A.

According to a first alternative form of the invention, R denotes a direct attachment to A, in which case R is the $4^{th}$ symbol.

According to this alternative form, R' can be a hydrogen atom or a carbon-based group which can contain at least one heteroatom.

According to a preferred embodiment of this alternative form, R' represents a carbon-based group containing from 1 to 20 carbon atoms, preferably an aliphatic group, more preferably an alkyl group which preferably contains from 1 to 12 carbon atoms.

According to a second alternative form of the invention, R' denotes a direct attachment to A, in which case R' is the $4^{th}$ symbol.

According to the first or the second alternative form, Z and Y can each be a hydrogen atom.

According to another embodiment of the first alternative form or of the second alternative form, Z and Y form, together with the carbon atoms to which they are attached, a ring. The ring formed by Z, Y and the atoms to which Z and Y are attached may or may not be substituted and can comprise at least one heteroatom. Z and Y can form, with the two carbon atoms to which they are attached, an aromatic nucleus. In this case, the imidazole ring can be a substituted or unsubstituted benzimidazole.

According to a third alternative form of the invention, of course when Y and Z do not form, together with the carbon atoms to which they are attached, a ring, Y or Z denotes a direct attachment to A, in which case Y or Z is the $4^{th}$ symbol.

According to a specific embodiment of the second or of the third alternative form of the invention, R represents a hydrogen atom or a carbon-based group which can contain at least one heteroatom.

According to this specific embodiment of the second alternative form or of the third alternative form of the invention, R can be a group of 1 to 20 carbon atoms, preferably an aliphatic group, more preferably an alkyl group preferably containing from 1 to 12 carbon atoms, more preferably still a methyl.

A can be a group containing up to 20 carbon atoms, which group can contain at least one heteroatom. A can be an aliphatic or aromatic group.

When A is an aliphatic group, A preferably contains from 1 to 20 carbon atoms, more preferably from 1 to 12 carbon atoms, more preferably still from 1 to 6 carbon atoms and very particularly from 1 to 3 carbon atoms. When A is an aromatic group, A preferably contains from 6 to 20 carbon atoms, more preferably from 6 to 12 carbon atoms.

Particularly suitable as divalent group A is an alkylene group containing from 1 to 20 carbon atoms, preferably from 1 to 12 carbon atoms, more preferably from 1 to 6 carbon atoms and more preferably still from 1 to 3 carbon atoms. Mention may be made, as divalent group A containing from 1 to 3 carbon atoms which is suitable, of the methylene group.

An arylene group preferably containing from 6 to 20 carbon atoms, more preferably from 6 to 12 carbon atoms, may also be suitable as divalent group A.

Very particularly suitable as 1,3-dipolar compounds are the compounds selected from the group consisting of nitrile oxides, nitrile imines and nitrones, in which case Q contains a —C≡N→O, —C≡N→N— or —C=N(→O)— unit.

According to the specific embodiment of the invention where Q comprises a —C≡N→O unit, Q preferably comprises, more preferably represents, the unit corresponding to the formula (III) in which four of the five symbols $R_1$ to $R_5$, which are identical or different, are each an atom or a group of atoms and the fifth symbol denotes a direct attachment to A, it being known that $R_1$ and $R_5$ are both other than H. The four of the five symbols $R_1$ to $R_5$ can be aliphatic or aromatic groups. The aliphatic groups can contain from 1 to 20 carbon atoms, preferably from 1 to 12 carbon atoms, more preferably from 1 to 6 carbon atoms and more preferably still from 1 to 3 carbon atoms. The aromatic groups can contain from 6 to 20 carbon atoms and preferably from 6 to 12 carbon atoms.

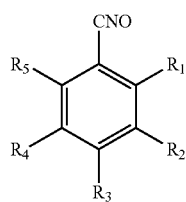

(III)

$R_1$, $R_3$ and $R_5$ are preferably each an alkyl group of 1 to 6 carbon atoms, more preferably of 1 to 3 carbon atoms, and more preferably still a methyl or ethyl group.

According to an alternative form of this specific embodiment of the invention, $R_1$, $R_3$ and $R_5$ are identical. According to this alternative form where they are identical, $R_1$, $R_3$ and $R_5$ are preferably each an alkyl group of 1 to 6 carbon atoms, more preferably of 1 to 3 carbon atoms, and more preferably still a methyl or ethyl group.

More preferably, the 1,3-dipolar compound is the compound 2,4,6-trimethyl-3-((2-methyl-1H-imidazol-1-yl) methyl)benzonitrile oxide, corresponding to the formula (IIIa), or the compound 2,4,6-triethyl-3-((2-methyl-1H-imidazol-1-yl)methyl)benzonitrile oxide, corresponding to the formula (IIIb):

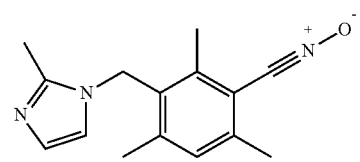

(IIIa)

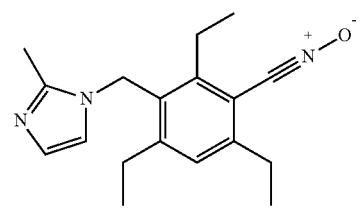

(IIIb)

According to the specific embodiment of the invention where Q comprises a —C=N(→O)— unit, Q preferably comprises, more preferably represents, the unit corresponding to the formula (IV) or (V):

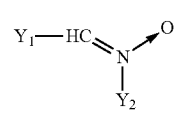

(IV)

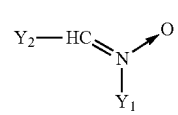

(V)

in which:

$Y_1$ is an aliphatic group, preferably an alkyl group preferably containing from 1 to 12 carbon atoms, or an aromatic group containing from 6 to 20 carbon atoms, preferably an alkylaryl group, more preferably a phenyl or tolyl group, and $Y_2$, comprising a direct attachment to A, is an aliphatic group, preferably an alkylene group preferably containing from 1 to 12 carbon atoms, or an aromatic group preferably containing from 6 to 20 carbon atoms and comprising, on its benzene nucleus, the direct attachment to A.

The direct attachment of the benzene nucleus of $Y_2$ to A amounts to saying that A is a substituent of the benzene nucleus of $Y_2$.

According to this specific embodiment of the invention, the 1,3-dipolar compound is the compound of formula (IVa), (IVb), (Va) or (Vb):

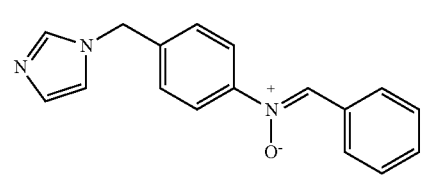

(IVa)

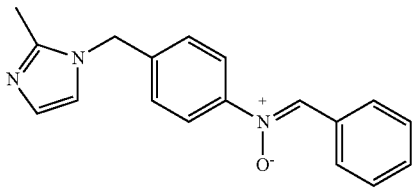
(IVb)

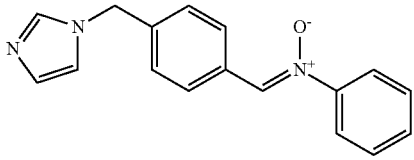
(Va)

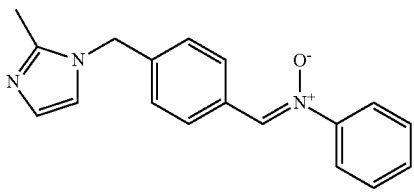
(Vb)

The amount of 1,3-dipolar compound introduced into the rubber composition is expressed as molar equivalent of imidazole ring. For example, if the 1,3-dipolar compound contains just one imidazole ring of formula (II) as defined above, one mole of imidazole ring corresponds to one mole of 1,3-dipolar compound. If the 1,3-dipolar compound contains two imidazole rings of formula (II) as defined above, two moles of imidazole ring correspond to one mole of 1,3-dipolar compound. In the latter case, the use of the 1,3-dipolar compound according to one molar equivalent of imidazole ring corresponds to a half-mole of 1,3-dipolar compound.

According to any one embodiment of the invention, the amount of 1,3-dipolar compound in the rubber composition is preferably between 0 and 3 molar equivalents, more preferably between 0 and 2 molar equivalents, more preferably still between 0 and 1 molar equivalent, indeed even more preferably still between 0 and 0.7 molar equivalent, of imidazole ring per 100 moles of monomer units constituting the diene elastomer. These preferred ranges make it possible to more finely optimize the compromise between the stiffness in the cured state and the hysteresis of the rubber composition according to its application, in particular in a tyre. For each of these preferred ranges, the lower limit is preferably at least 0.1 molar equivalent of 1,3-dipolar compound.

The rubber composition in accordance with the invention comprises any type of "reinforcing" filler known for its abilities to reinforce a rubber composition which can be used for the manufacture of tyres, for example an organic filler, such as carbon black, a reinforcing inorganic filler, such as silica, with which is combined, in a known way, a coupling agent, or also a mixture of these two types of filler.

Such a reinforcing filler typically consists of nanoparticles, the (weight-)average size of which is less than a micrometer, generally less than 500 nm, usually between 20 and 200 nm, in particular and more preferably between 20 and 150 nm.

All carbon blacks, in particular the blacks conventionally used in tyres or their treads ("tyre-grade" blacks), are suitable as carbon blacks. Among the latter, mention will more particularly be made of the reinforcing carbon blacks of the 100, 200 and 300 series, or the blacks of the 500, 600 or 700 series (ASTM grades), such as, for example, the N115, N134, N234, N326, N330, N339, N347, N375, N550, N683 and N772 blacks. These carbon blacks can be used in the isolated state, as available commercially, or in any other form, for example as support for some of the rubber additives used.

The term "reinforcing inorganic filler" should be understood here as meaning any inorganic or mineral filler, whatever its colour and its origin (natural or synthetic), also known as "white filler", "clear filler" or even "non-black filler", in contrast to carbon black, capable of reinforcing, by itself alone, without means other than an intermediate coupling agent, a rubber composition intended for the manufacture of pneumatic tyres, in other words capable of replacing, in its reinforcing role, a conventional tyre-grade carbon black; such a filler is generally characterized, in a known way, by the presence of hydroxyl (—OH) groups at its surface.

Mineral fillers of the siliceous type, preferably silica ($SiO_2$), are suitable in particular as reinforcing inorganic fillers. The silica used can be any reinforcing silica known to a person skilled in the art, in particular any precipitated or fumed silica exhibiting a BET specific surface and a CTAB specific surface both of less than 450 $m^2/g$, preferably from 30 to 400 $m^2/g$, in particular between 60 and 300 $m^2/g$. Mention will be made, as highly dispersible precipitated silicas ("HDSs"), for example, of the Ultrasil 7000 and Ultrasil 7005 silicas from Degussa, the Zeosil 1165MP, 1135MP and 1115MP silicas from Rhodia, the Hi-Sil EZ150G silica from PPG, the Zeopol 8715, 8745 and 8755 silicas from Huber or the silicas having a high specific surface as described in Application WO 03/016387.

In the present account, the BET specific surface is determined in a known way by gas adsorption using the Brunauer-Emmett-Teller method described in *The Journal of the American Chemical Society*, Vol. 60, page 309, February 1938, more specifically, according to French Standard NF ISO 9277 of December 1996 (multipoint (5 point) volumetric method—gas: nitrogen—degassing: 1 hour at 160° C.—relative pressure p/po range: 0.05 to 0.17). The CTAB specific surface is the external surface determined according to French Standard NF T 45-007 of November 1987 (method B).

The physical state under which the reinforcing inorganic filler is provided is not important, whether it is in the form of a powder, microbeads, granules or also beads. Of course, the expression "reinforcing inorganic filler" is also understood to mean mixtures of different reinforcing inorganic fillers, in particular of highly dispersible silicas as described above.

A person skilled in the art will understand that use might be made, as filler equivalent to the reinforcing inorganic filler described in the present section, of a reinforcing filler of another nature, in particular organic nature, such as carbon black, provided that this reinforcing filler is covered with an inorganic layer, such as silica, or else comprises, at its surface, functional sites, in particular hydroxyl sites, requiring the use of a coupling agent in order to establish the bond between the filler and the elastomer. Mention may be made, by way of example, for example, of carbon blacks for tyres, such as described, for example, in patent documents WO 96/37547 and WO 99/28380.

According to a specific embodiment of the invention, the inorganic filler, preferably a silica, represents more than 50% by weight of the weight of the reinforcing filler of the rubber composition. It is then said that the reinforcing inorganic filler is predominant.

When it is combined with a predominant reinforcing inorganic filler, such as silica, the carbon black is preferably used at a content of less than 20 phr, more preferably of less than 10 phr (for example, between 0.5 and 20 phr, in particular between 2 and 10 phr). Within the intervals indicated, the colouring properties (black pigmenting agent) and UV-stabilizing properties of the carbon blacks are benefited from, without, moreover, adversely affecting the typical performances contributed by the reinforcing inorganic filler.

The content of total reinforcing filler is preferably between 30 and 160 phr, more preferably between 40 and 160 phr. Below 30 phr, the reinforcement of the rubber composition can be insufficient to contribute an appropriate level of cohesion or wear resistance of the rubber component of the tyre comprising this composition. More preferably still, the content of total reinforcing filler is at least 50 phr. Above 160 phr, there exists a risk of increasing the hysteresis and thus the rolling resistance of the tyres. For this reason, the content of total reinforcing filler is preferably within a range extending from 50 to 120 phr, in particular for use in a tyre tread. Any one of these ranges of content of total reinforcing filler applies to any one of the embodiments of the invention.

In order to couple the reinforcing inorganic filler to the diene elastomer, use is made, in a well-known way, of an at least bifunctional coupling agent, in particular a silane, (or bonding agent) intended to provide a satisfactory connection, of chemical and/or physical nature, between the inorganic filler (surface of its particles) and the diene elastomer. Use is made in particular of at least bifunctional organosilanes or polyorganosiloxanes.

Use is made in particular of silane polysulphides, referred to as "symmetrical" or "unsymmetrical" depending on their specific structure, such as described, for example, in Applications WO 03/002648 (or US 2005/016651) and WO 03/002649 (or US 2005/016650).

Particularly suitable, without the definition below being limiting, are silane polysulphides corresponding to the general formula (V):

Z-A-S$_x$-A-Z (V)

in which:
x is an integer from 2 to 8 (preferably from 2 to 5);
the A symbols, which are identical or different, represent a divalent hydrocarbon radical (preferably a $C_1$-$C_{18}$ alkylene group or a $C_6$-$C_{12}$ arylene group, more particularly a $C_1$-$C_{10}$, in particular $C_1$-$C_4$, alkylene, especially propylene);
the Z symbols, which are identical or different, correspond to one of the three formulae below:

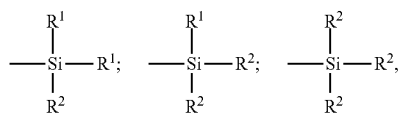

in which:
the $R^1$ radicals, which are substituted or unsubstituted and identical to or different from one another, represent a $C_1$-$C_{18}$ alkyl, $C_5$-$C_{18}$ cycloalkyl or $C_6$-$C_{18}$ aryl group (preferably $C_1$-$C_6$ alkyl, cyclohexyl or phenyl groups, in particular $C_1$-$C_4$ alkyl groups, more particularly methyl and/or ethyl);
the $R^2$ radicals, which are substituted or unsubstituted and identical to or different from one another, represent a $C_1$-$C_{18}$ alkoxyl or $C_5$-$C_{18}$ cycloalkoxyl group (preferably a group chosen from $C_1$-$C_8$ alkoxyls and $C_5$-$C_8$ cycloalkoxyls, more preferably still a group chosen from $C_1$-$C_4$ alkoxyls, in particular methoxyl and ethoxyl).

In the case of a mixture of alkoxysilane polysulphides corresponding to the above formula (I), in particular normal commercially available mixtures, the mean value of the "x" indices is a fractional number preferably of between 2 and 5, more preferably of approximately 4. However, the invention can also advantageously be carried out, for example, with alkoxysilane disulphides (x=2).

Mention will more particularly be made, as examples of silane polysulphides, of bis(($C_1$-$C_4$)alkoxyl($C_1$-$C_4$)alkylsilyl($C_1$-$C_4$)alkyl) polysulphides (in particular disulphides, trisulphides or tetrasulphides), such as, for example, bis(3-trimethoxysilylpropyl) or bis(3-triethoxysilylpropyl) polysulphides. Use is made in particular, among these compounds, of bis(3-triethoxysilylpropyl) tetrasulphide, abbreviated to TESPT, of formula $[(C_2H_5O)_3Si(CH_2)_3S_2]_2$, or bis(3-triethoxysilylpropyl) disulphide, abbreviated to TESPD, of formula $[(C_2H_5O)_3Si(CH_2)_3S]_2$.

Mention will in particular be made, as coupling agent other than alkoxysilane polysulphide, of bifunctional POSs (polyorganosiloxanes), or else of hydroxysilane polysulphides, such as described in Patent Applications WO 02/30939 (or U.S. Pat. No. 6,774,255) and WO 02/31041 (or US 2004/051210), or else of silanes or POSs bearing azodicarbonyl functional groups, such as described, for example, in Patent Applications WO 2006/125532, WO 2006/125533 and WO 2006/125534.

Of course, use might also be made of mixtures of the coupling agents described above, as described in particular in the abovementioned Application WO 2006/125534.

The content of coupling agent is advantageously less than 20 phr, it being understood that it is generally desirable to use as little as possible thereof. Typically, the content of coupling agent represents from 0.5% to 15% by weight, with respect to the amount of inorganic filler. Its content is preferably between 0.5 and 12 phr, more preferably within a range extending from 3 to 10 phr. This content is easily adjusted by a person skilled in the art depending on the content of inorganic filler used in the composition.

The rubber composition in accordance with the invention can also comprise, in addition to the coupling agents, coupling activators, agents for covering the inorganic fillers or more generally processing aids capable, in a known way, by virtue of an improvement in the dispersion of the filler in the rubber matrix and of a lowering of the viscosity of the compositions, of improving their ability to be processed in the raw state.

The rubber composition in accordance with the invention can also comprise all or a portion of the usual additives generally used in the elastomer compositions intended to constitute external mixtures of finished rubber articles, such as tyres, in particular treads, such as, for example, plasticizers or extending oils, whether the latter are aromatic or non-aromatic in nature, in particular very weakly aromatic or non-aromatic oils (e.g., paraffin oils, hydrogenated naphthenic oils, MES oils or TDAE oils), vegetable oils, in particular glycerol esters, such as glycerol trioleates, plasticizing hydrocarbon resins exhibiting a high Tg, preferably of greater than 30° C., such as described, for example, in Applications WO 2005/087859, WO 2006/061064 and WO 2007/017060, pigments, protection agents, such as antiozone waxes, chemical antiozonants or antioxidants, antifatigue agents, reinforcing resins (such as resorcinol or bismaleimide), methylene acceptors (for example phenolic novolak resin) or methylene donors (for example HMT or H3M), such as described, for example, in Application WO 02/10269, a crosslinking system, vulcanization accelerators or retarders, or vulcanization activators. The crosslinking system is preferably based on sulphur but it can also be based on sulphur donors, on peroxide, on bismaleimides or on their mixtures.

The rubber composition in accordance with the invention is manufactured in appropriate mixers, using two successive phases of preparation well known to a person skilled in the art: a first phase of thermomechanical working or kneading ("non-productive" phase) at high temperature, up to a maximum temperature of between 130° C. and 200° C., followed by a second phase of mechanical working ("productive" phase) up to a lower temperature, typically below 110° C., for example between 40° C. and 100° C., during which finishing phase the crosslinking system is incorporated.

The process for preparing the rubber composition in accordance with the invention and based on at least one crosslinking system comprises the following stages:
  adding, during a first "non-productive" stage, to the diene elastomer, the 1,3-dipolar compound, the reinforcing filler and, if appropriate, the coupling agent, by kneading thermomechanically until a maximum temperature of between 130° C. and 200° C. is reached,
  cooling the combined mixture to a temperature of less than 100° C.,
  subsequently incorporating the crosslinking system,
  kneading everything up to a maximum temperature of less than 120° C.

The amount of 1,3-dipolar compound added is preferably between 0 and 3 molar equivalents, more preferably between 0 and 2 molar equivalents, more preferably still between 0 and 1 molar equivalent, indeed even more preferably still between 0 and 0.7 molar equivalent, of imidazole ring per 100 moles of monomer units constituting the diene elastomer. For each of these preferred ranges, the lower limit is preferably at least 0.1 molar equivalent of 1,3-dipolar compound.

According to a preferred embodiment of the invention, the 1,3-dipolar compound is incorporated in the diene elastomer before the introduction of the other constituents of the rubber composition. The contact time between the diene elastomer and the 1,3-dipolar compound which are thermomechanically kneaded is adjusted as a function of the conditions of the thermomechanical kneading, in particular as a function of the temperature. The higher the temperature of the kneading, the shorter this contact time. Typically, it is from 1 to 5 minutes for a temperature of 100° C. to 130° C.

According to this preferred embodiment of the invention, at least one antioxidant is preferably added to the diene elastomer before it is introduced into a mixer, in particular at the end of the synthesis of the diene elastomer, as is done conventionally.

After the incorporation of all the ingredients of the rubber composition, the final composition thus obtained is subsequently calendered, for example in the form of a sheet or plaque, in particular for laboratory characterization, or else extruded, in order to form, for example, a rubber profiled element used as rubber component in the preparation of the tyre.

Thus, according to a specific embodiment of the invention, the rubber composition in accordance with the invention, which can either be in the raw state (before crosslinking or vulcanization) or in the cured state (after crosslinking or vulcanization), is in a tyre, in particular in a tyre tread.

The abovementioned characteristics of the present invention, and also others, will be better understood on reading the following description of several implementational examples of the invention, given by way of illustration and without limitation.

II. IMPLEMENTATIONAL EXAMPLES OF THE INVENTION

II.1-Measurements and Tests Used

NMR Analysis:

The structural analysis and also the determination of the molar purities of the molecules synthesized are carried out by an NMR analysis. The spectra are acquired on a Bruker Avance 3400 MHz spectrometer equipped with a 5 mm BBFO Z-grad "broad band" probe. The quantitative $^1$H NMR experiment uses a simple 30° pulse sequence and a repetition time of 3 seconds between each of the 64 acquisitions. The samples are dissolved in deuterated dimethyl sulphoxide (DMSO). This solvent is also used for the lock signal. Calibration is carried out on the signal of the protons of the deuterated DMSO at 2.44 ppm with respect to a TMS reference at 0 ppm. The $^1$H NMR spectrum coupled with the 2D $^1$H/$^{13}$C HSQC and $^1$H/$^{13}$C HMBC experiments make possible the structural determination of the molecules (cf. tables of assignments). The molar quantifications are carried out from the quantitative 1D $^1$H NMR spectrum.

Tensile Tests:

These tensile tests make it possible to determine the elasticity stresses. Unless otherwise indicated, they are carried out in accordance with French Standard NF T 46-002 of September 1988. Processing the tensile recordings also makes it possible to plot the curve of modulus as a function of the elongation. At first elongation, the nominal secant modulus, calculated by reducing to the initial cross-section of the test specimen, (or apparent stress, in MPa) is measured at 100% elongation, denoted ASM100.

All these tensile measurements are carried out under the standard temperature conditions (23±2° C.) according to Standard NF T 46-002.

Dynamic Properties:

The dynamic properties tan(δ)max are measured on a viscosity analyser (Metravib VA4000) according to Standard ASTM D 5992-96. The response of a sample of vulcanized composition (cylindrical test specimen with a thickness of 4 mm and a cross-section of 400 mm$^2$), subjected to a simple alternating sinusoidal shear stress, at a frequency of 10 Hz, under standard temperature conditions (23° C.) according to Standard ASTM D 1349-99 or, as the case may be, at a different temperature (100° C.), is recorded. A strain amplitude sweep is carried out from 0.1% to 100% (outward cycle) and then from 100% to 0.1% (return cycle). The results made use of are the complex dynamic shear modulus (G*) at 25% strain, the loss factor tan(δ) and the difference in modulus (ΔG*) between the values at 0.1% and 100% strain (Payne effect). For the return cycle, the maximum value of tan(δ) observed, denoted tan(δ)max, is indicated.

II.2-Synthesis of the 1,3-dipolar compound 2,4,6-trimethyl-3-((2-methyl-1H-imidazol-1-yl)methyl) benzonitrile oxide This compound can be prepared according to the following reaction scheme:

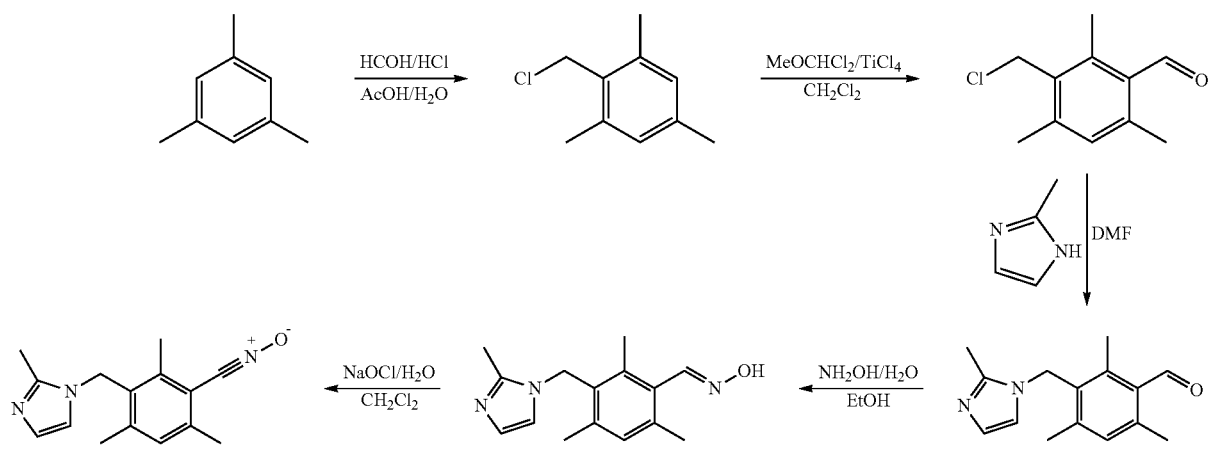
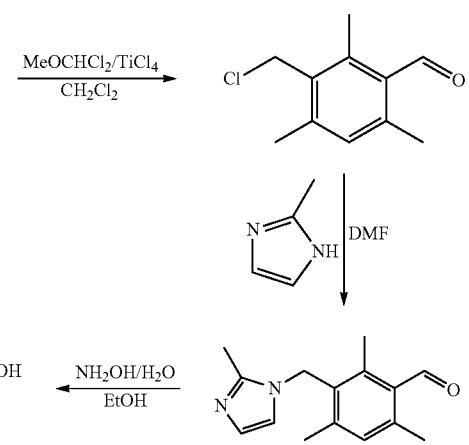

II.2-1-Synthesis of 2-(chloromethyl)-1,3,5-trimethylbenzene

This compound can be obtained according to a procedure described in the following paper: Zenkevich, I. G. and Makarov, A. A., Russian Journal of General Chemistry, Vol. 77, No. 4 (2007), pp. 611-619 (Zhurnal Obshchei Khimii, Vol. 77, No. 4 (2007), pp. 653-662).

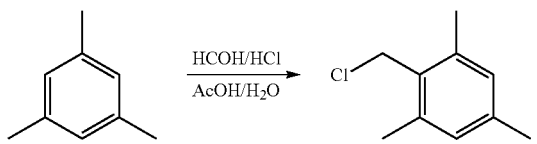

A mixture of mesitylene (100.0 g, 0.832 mol), paraformaldehyde (26.2 g, 0.874 mol) and hydrochloric acid (240 ml, 37%, 2.906 mol) in acetic acid (240 ml) is stirred and heated very slowly (1.5 hours) up to 37° C. After returning to ambient temperature, the mixture is diluted with water (1.0 l) with $CH_2Cl_2$ (200 ml) and the product is extracted with $CH_2Cl_2$ (4 times with 50 ml). The organic phases are combined, then washed with water (5 times with 100 ml) and evaporated down to 11-12 mbar (temperature of the bath=42° C.). A colourless oil (133.52 g, yield 95%) is obtained. After 15-18 hours at +4° C., the oil crystallized. The crystals are filtered off, washed with petroleum ether cooled to −18° C. (40 ml) and then dried under atmospheric pressure at ambient temperature for 3 to 5 hours. A white solid (95.9 g, yield 68%) with a melting point of 39° C. is obtained. The molar purity is greater than 96% ($^1$H NMR).

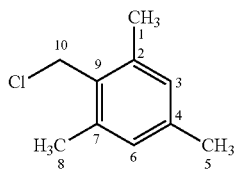

| No. | δ $^1$H (ppm) | δ $^{13}$C (ppm) |
|---|---|---|
| 1/8 | 2.27 | 18.4 |
| 2/7 | — | 136.9 |
| 3/6 | 6.81 | 128.5 |
| 4 | — | 137.4 |
| 5 | 2.15 | 20.3 |
| 9 | — | 130.5 |
| 10 | 4.69 | 41.3 |

II.2-2-Synthesis of 3-(chloromethyl)-2,4,6-trimethylbenzaldehyde

This compound can be obtained according to a procedure described in the following paper: Yakubov, A. P., Tsyganov, D. V., Belen'kii, L. I. and Krayushkin, M. M., Bulletin of the Academy of Sciences of the USSR, Division of Chemical Science (English Translation), Vol. 40, No. 7.2 (1991), pp. 1427-1432 (Izvestiya Akademii Nauk SSSR, Seriya Khimicheskaya; No. 7 (1991), pp. 1609-1615).

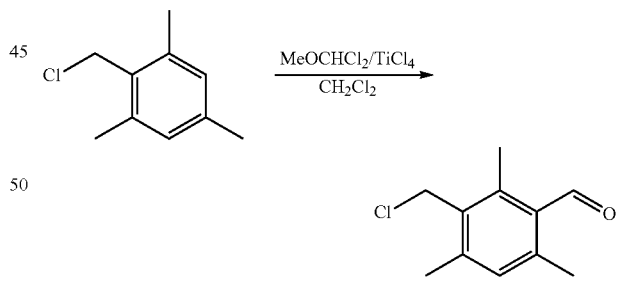

A solution of 2-(chloromethyl)-1,3,5-trimethylbenzene (20.0 g, 0.118 mol) and dichloromethyl methyl ether (27.26 g, 0.237 mol) in dichloromethane (200 ml) is added under argon over 10-12 minutes to a solution of $TiCl_4$ (90.0 g, 0.474 mol) in dichloromethane (200 ml) at 17° C. After stirring at 17-20° C. for 15-20 minutes, water (1000 ml) and ice (500 g) are added to the reaction medium. After stirring for 10-15 minutes, the organic phase is separated. The aqueous phase is extracted with $CH_2Cl_2$ (3 times with 75 ml). The combined organic phases are washed with water (4 times with 100 ml) and evaporated under reduced pressure to result in a solid (temperature of the bath=28° C.). The target product (22.74 g) is obtained with a yield of 97%. Its melting point is 58° C. The molar purity, estimated by $^1$H NMR, is 95 mol %.

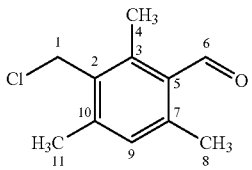

| No. | δ $^1$H (ppm) | δ $^{13}$C (ppm) |
|---|---|---|
| 1 | 4.77 | 40.6 |
| 2 | — | 132.9 |
| 3 | — | 139.5 |
| 4 | 2.51 | 14.4 |
| 5 | — | 131.4 |
| 6 | 10.43 | 194.2 |
| 7 | — | 140.1 |
| 8 | 2.41 | 19.3 |
| 9 | 6.99 | 131.2 |
| 10 | — | 142.4 |
| 11 | 2.34 | 19.8 |

II.2-3-Synthesis of 2,4,6-trimethyl-3-((2-methyl-1H-imidazol-1-yl)methyl)benzaldehyde

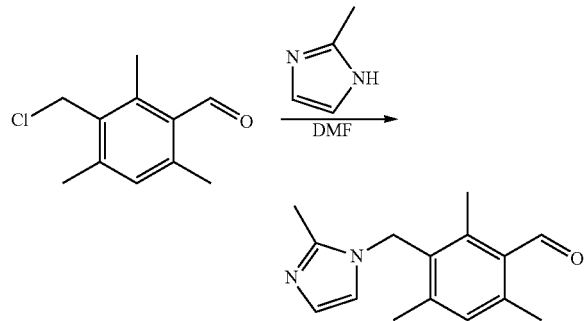

A mixture of 3-(chloromethyl)-2,4,6-trimethylbenzaldehyde (10.0 g, 0.051 mol) and imidazole (10.44 g, 0.127 mol) in DMF (10 ml) is stirred at 80° C. for one hour.

After returning to 40-50° C., the mixture is diluted with water (200 ml) and stirred for 10 minutes. The precipitate obtained is filtered off, washed on the filter with water (4 times with 25 ml) and then dried at ambient temperature. A white solid (7.92 g, yield 64%) with a melting point of 161° C. is obtained. The molar purity is 91% ($^1$H NMR).

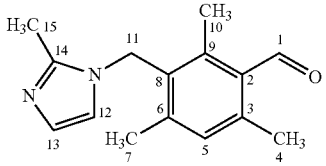

| No. | δ $^1$H (ppm) | δ $^{13}$C (ppm) |
|---|---|---|
| 1 | 10.45 | 194.2 |
| 2 | — | 131.5 |
| 3 | — | 139.5 |
| 4 | 2.44 | 19.6 |
| 5 | 7.04 | 131.2 |
| 6 | — | 142.5 |
| 7 | 2.19 | 19.5 |
| 8 | — | 131 |
| 9 | — | 139.5 |
| 10 | 2.34 | 14.6 |
| 11 | 5.02 | 42.5 |
| 12 | 6.24 | 116.9 |
| 13 | 6.59 | 125.9 |
| 14 | — | 143.5 |
| 15 | 2.32 | 12.7 |

II.2-4-Synthesis of 2,4,6-trimethyl-3-((2-methyl-1H-imidazol-1-yl)methyl)benzaldehyde oxime

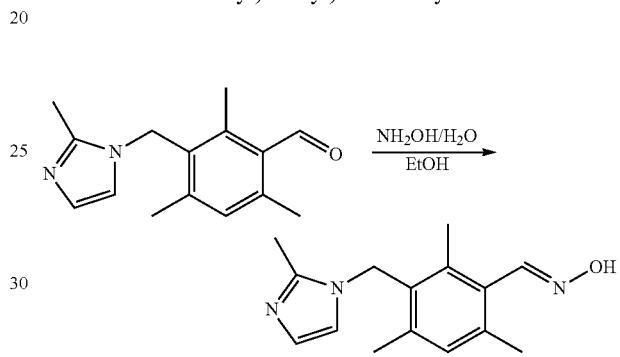

An aqueous hydroxylamine solution (809 g, 0.134 mol, 50% in water, Aldrich) in EtOH (10 ml) is added to a solution of 2,4,6-trimethyl-3-((2-methyl-1H-imidazol-1-yl)methyl)benzaldehyde (20.3 g, 0.084 mol) in EtOH (110 ml) at 40° C. The reaction medium is stirred at a temperature of 50 to 55° C. for 2.5 hours. After returning to 23° C., the precipitate obtained is filtered off, washed twice on the filter with an EtOH/H$_2$O (10 ml/15 ml) mixture and dried under atmospheric pressure at ambient temperature for 15 to 20 hours. A white solid (19.57 g, yield 91%) with a melting point of 247° C. is obtained. The molar purity is greater than 87% ($^1$H NMR).

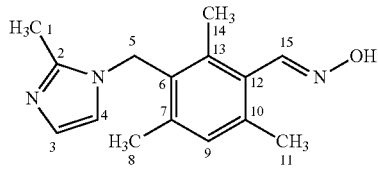 [SMILES: Cc1cc(C)c(Cn2ccnc2C)c(C)c1/C=N/O]

| No. | δ $^1$H (ppm) | δ $^{13}$C (ppm) |
|---|---|---|
| 1 | 2.31 | 12.7 |
| 2 | — | 143.4 |
| 3 | 6.58 | 125.8 |
| 4 | 6.22 | 116.9 |
| 5 | 4.97 | 43.2 |
| 6 | — | 129.3 |
| 7 | — | 136.2 |
| 8 | 2.23 | 20.2 |

-continued

| No. | δ ¹H (ppm) | δ ¹³C (ppm) |
|---|---|---|
| 9 | 6.97 | 130 |
| 10 | — | 137.3 |
| 11 | 2.15 | 19.1 |
| 12 | — | 129.1 |
| 13 | — | 136.1 |
| 14 | 2.11 | 15.9 |
| 15 | 8.25 | 147.4 |
| OH | 11.11 | — |

II.2-5-Synthesis of 2,4,6-trimethyl-3-((2-methyl-1H-imidazol-1-yl)methyl)benzonitrile oxide

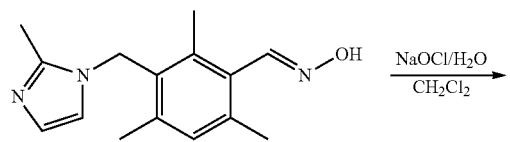

An aqueous solution of NaOCl (4% of active chlorine, Aldrich, 49 ml) is added dropwise over 5 minutes to a mixture of 2,4,6-trimethyl-3-((2-methyl-1H-imidazol-1-yl)methyl)benzaldehyde oxime (8.80 g, 0.034 mol) in CH$_2$Cl$_2$ (280 ml) at 6° C. The temperature of the reaction medium is maintained between 6° C. and 8° C. The reaction medium is subsequently stirred at 8° C. to 21° C. for 2 hours. The organic phase is separated. The organic phase is washed with water (3 times with 50 ml). After concentrating under reduced pressure (temperature of the bath=22-23° C., 220 mbar), petroleum ether (10 ml) is added, the solvent is evaporated down to 8-10 ml and the solution is maintained at −18° C. for 10-15 hours, so as to obtain a precipitate. The precipitate is filtered off, washed on the filter with the CH$_2$Cl$_2$/petroleum ether (2 ml/6 ml) mixture and then with petroleum ether (2 times 10 ml), and finally dried under atmospheric pressure at ambient temperature for 10-15 hours. A white solid (5.31 g, yield 61%) with a melting point of 139° C. is obtained.

The molar purity is greater than 95 mol % (¹H NMR).

| No. | δ ¹H (ppm) | δ ¹³C (ppm) |
|---|---|---|
| 1 | 2.3 | 12.6 |
| 2 | — | 143.6 |
| 3 | 6.59 | 126.1 |
| 4 | 6.27 | 117.1 |
| 5 | 4.99 | 43 |
| 6 | — | 130.6 |
| 7 | — | 140.7 |
| 8 | 2.16 | 19.2 |
| 9 | 7.12 | 129.9 |
| 10 | — | 141 |
| 11 | 2.34 | 20 |
| 12 | — | 112.1 |
| 13 | — | NI |
| 14 | — | 140.8 |
| 15 | 2.28 | 17.7 |

II.3-Synthesis of the 1,3-dipolar compound 2,4,6-trimethyl-3-((2-methyl-1H-benzo[d]imidazol-1-yl)methyl)benzonitrile oxide II.3-1-Synthesis of 2-(chloromethyl)-1,3,5-trimethylbenzene The synthesis is identical to that described in section II.2-1.

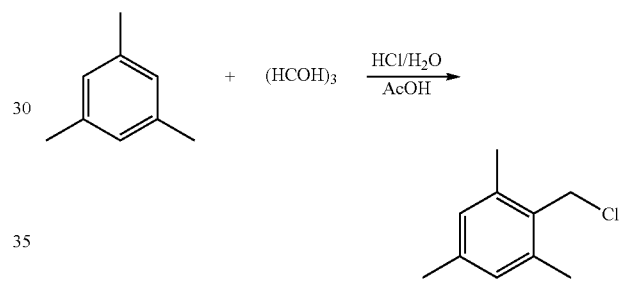

II.3-2-Synthesis of 3-(chloromethyl)-2,4,6-trimethylbenzaldehyde

The synthesis is identical to that described in section II.2-2.

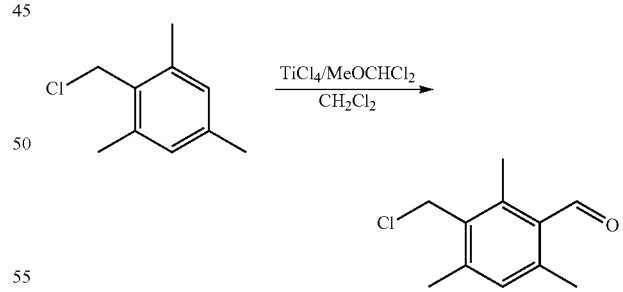

II.3-3-Synthesis of 2,4,6-trimethyl-3-((2-methyl-1H-benzo[d]imidazol-1-yl)methyl)benzaldehyde

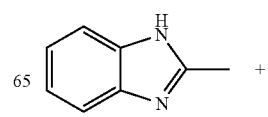

-continued

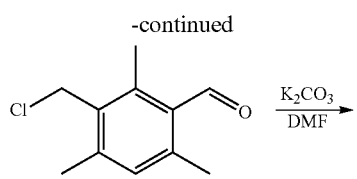

A mixture of aldehyde (11.9 g, 60.5 mmol), 2-methylbenzimidazole (8.00 g, 60.5 mmol) and potassium carbonate (6.27 g, 45.4 mmol) in DMF (dimethylformamide, 15 ml) is stirred at 80° C. for one hour and at 90° C. for three hours. The mixture is subsequently diluted with water (600 ml). The organic phase is extracted with EtOAc (3 times 150 ml) and washed with water (4 times 75 ml). The solvents are evaporated under reduced pressure (36° C. ($T_{bath}$)) to result in a brown oil. The latter is crystallized from petroleum ether 40/60 (15 ml) and ethyl acetate (20 ml).

A solid (11.70 g, 40.0 mmol, yield 66%) with a melting point of 118° C. is obtained. The molar purity is 70%, EtOAc—5% ($^1$H NMR).

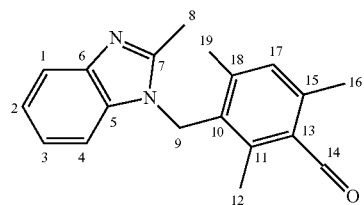

Solvent: DMSO

| No. | δ $^1$H (ppm) | δ $^{13}$C (ppm) |
|---|---|---|
| 1 | 7.45 | 118.0 |
| 2 | 7.01 | 120.5 |
| 3 | 6.93 | 121.2 |
| 4 | 6.79 | 109.6 |
| 5 | / | 134.9 |
| 6 | / | 142.1 |
| 7 | / | 151.8 |
| 8 | 2.38 | 14.1 |
| 9 | 5.42 | 42.6 |
| 10 | / | ~131 |
| 11 | / | 139.4 |
| 12 | 2.28 | 15.1 |
| 13 | / | 131.7 |
| 14 | 10.44 | 194.3 |
| 15 | / | 142.4 |
| 16 | ~2.44 | 19.8 |
| 17 | 7.04 | 131.2 |
| 18 | / | ~141.8 |
| 19 | 2.18 | 20.3 |

II.3-4-Synthesis of 2,4,6-trimethyl-3-((2-methyl-1H-benzo[d]imidazol-1-yl)methyl)benzaldehyde oxime

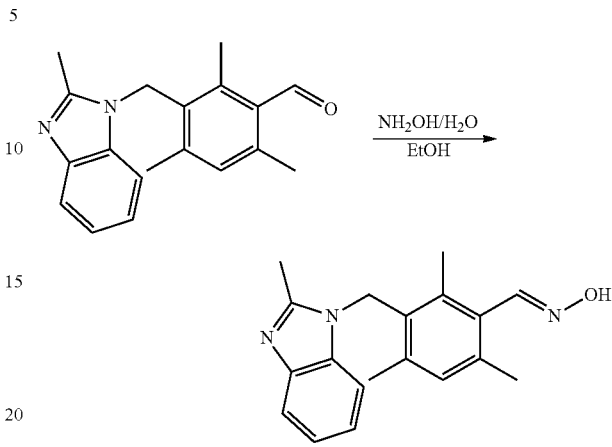

A hydroxylamine solution (6.14 g, 62.9 mmol, 50% in water, Aldrich) in EtOH (20 ml) is added to a solution of aldehyde (11.5 g, 39.4 mmol) in EtOH (80 ml) at 35° C. The reaction medium is stirred at 48-50° C. for 3.5 hours. The reaction medium is subsequently cooled down to 10-15° C. and the precipitate obtained is filtered off, washed on the filter with a mixture of ethanol and water (twice with 5 ml and 10 ml mixture) and then dried under atmospheric pressure at ambient temperature for 15-20 hours.

A solid (7.95 g, 25.9 mmol, yield 66%) with a melting point of 248° C. is obtained. The molar purity is greater than 80% ($^1$H NMR).

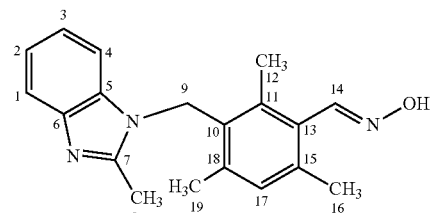

| No. | δ $^1$H (ppm) | δ $^{13}$C (ppm) |
|---|---|---|
| 1 | 7.43 | 117.8 |
| 2 | 7.01 | 120.3 |
| 3 | 6.91 | 121 |
| 4 | 6.78 | 109.6 |
| 5 | / | 134.9 |
| 6 | / | 142 |
| 7 | / | 151.7 |
| 8 | 2.37 | 14 |
| 9 | 5.37 | 43.1 |
| 10/11/13/18 | / | between 129.3 and 136.2 |
| 12 | 2.06 | 16.3 |
| 14 | 8.24 | 147.3 |
| 15 | / | 137.1 |
| 16 | 2.23 | 20.3 |
| 17 | 6.96 | 130.1 |
| 19 | 2.12 | 19.6 |

II.3-5-Synthesis of 2,4,6-trimethyl-3-((2-methyl-1H-benzo[d]imidazol-1-yl)methyl)benzonitrile oxide

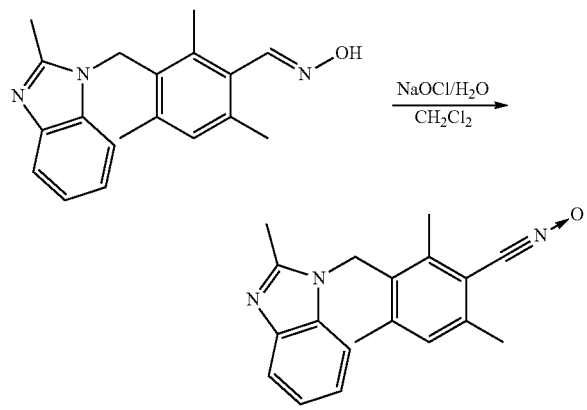

An aqueous solution of NaOCl (6% of active chlorine) (25.4 ml) is added dropwise over 6-8 minutes to a solution of oxime (6.20 g, 20.2 mmol) in dichloromethane (150 ml) cooled down to 5° C. The reaction medium is stirred for 4.5 hours until an emulsion is formed at 10° C. The organic phase is separated and washed with water (3 times with 25 ml). After evaporation of the solvent under reduced pressure ($T_{bath}$ 22-23° C.) until crystallization occurs, petroleum ether (40/60) (10 ml) and dichloromethane (4 ml) are added. The suspension is stirred for 10-15 minutes and the precipitate is filtered off, washed on the filter with the $CH_2Cl_2$/petroleum ether (2 ml/4 ml) mixture and with petroleum ether (40/60) (6 ml), and finally dried under atmospheric pressure at ambient temperature for 10-15 hours.

A white solid (4.85 g, 15.9 mmol, yield 79%) with a melting point of 142° C. is obtained. The molar purity is greater than 71% ($^1$H NMR).

The crude product (4.4 g) is redissolved in acetone (100 ml), this solution is then poured into water (500 ml) and the suspension is stirred for 5-10 minutes. The precipitate is filtered off, washed on the filter with water (200 ml) and dried under atmospheric pressure at ambient temperature for 10-15 hours.

A white solid (3.82 g, 12.6 mmol, yield 62%) with a melting point of 136.5-137.5° C. is obtained with a purity of 94 mol % by $^1$H NMR.

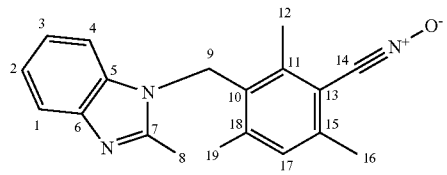 [SMILES: Cc1cc(C)c(Cn2c(C)nc3ccccc32)c(C)c1C#[N+][O-]]

| No. | δ $^1$H (ppm) | δ $^{13}$C (ppm) |
|---|---|---|
| 1 | 7.45 | 118.2 |
| 2 | 7.02 | 120.7 |
| 3 | 6.95 | 121.2 |
| 4 | 6.81 | 109.6 |
| 5 | / | 134.7 |
| 6 | / | 141.9 |
| 7 | / | 151.7 |
| 8 | 2.36 | 13.9 |
| 9 | 5.39 | 42.8 |
| 10 | / | 130.5 |
| 11 | / | between 140.2 and 140.6 |
| 12 | 2.24 | 18.0 |
| 13 | / | 112.3 |
| 14 | / | Undetected |
| 15 | / | 140.9 |
| 16 | 2.34 | 19.9 |
| 17 | / | 130.2 |
| 18 | / | between 140.2 and 140.6 |
| 19 | 2.1 | 19.7 |

Solvent: DMSO

II.4-Preparation of the Rubber Compositions

Use is made of the 1,3-dipolar compounds, the synthesis of which is described above.

These compositions are manufactured in the following way: the elastomer, if appropriate the 1,3-dipolar compound, which is kneaded alone with the elastomer at 110° C. for approximately 2 minutes, then the silica, the coupling agent and also the various other ingredients, with the exception of the vulcanization system, are introduced into an internal mixer (final degree of filling: approximately 70% by volume), the initial vessel temperature of which is approximately 110° C. Thermomechanical working (non-productive phase) is then carried out in one stage, which lasts approximately 5 min to 6 min, until a maximum "dropping" temperature of 160° C. is reached. The mixture thus obtained is recovered and cooled and then sulphur and an accelerator of sulphonamide type are incorporated on a mixer (homofinisher) at 23° C., everything being mixed (productive phase) for an appropriate time (for example between 5 and 12 min).

The compositions thus obtained are subsequently calendered, either in the form of plaques (with a thickness ranging from 2 to 3 mm) or thin sheets of rubber, for the measurement of their physical or mechanical properties, or in the form of profiled elements which can be used directly, after cutting and/or assembling to the desired dimensions, for example as semi-finished products for tyres, in particular for treads.

The crosslinking is carried out at 150° C. The crosslinking time, $t'_c(90)$, is the time necessary for the torque of the composition to reach 90% of the maximum torque of the composition. The torques of the composition are measured at 150° C. with an oscillating disc rheometer, according to Standard DIN 53529-Part 3 (June 1983). $t'_c(90)$ is determined according to Standard NF T 43-015 for each of the compositions. It varies approximately from 20 to 40 minutes from one composition to another.

II.4-1 Example 1

The formulations (in phr) of the compositions A, B, C and D are described in Table I. The compositions A and B, based on SBR and silica, differ in that the composition B contains the 1,3-dipolar compound, the synthesis of which is described in section II.2. The compositions C and D, based on polyisoprene and silica, differ in that the composition D contains the 1,3-dipolar compound.

The compositions B and D are in accordance with the invention. The compositions A and C are not in accordance with the invention and are the respective control compositions for the compositions B and D.

TABLE I

| | Composition | | | |
|---|---|---|---|---|
| | A not in accordance | B in accordance | C not in accordance | D in accordance |
| SBR (1) | 100 | 100 | — | — |
| IR (2) | — | — | 100 | 100 |
| 1,3-Dipolar compound (3) | — | 1.16 | — | 1.16 |
| Carbon black N234 | 3 | 3 | 3 | 3 |
| Silica (4) | 55 | 55 | 55 | 55 |
| Silane (5) | 5.5 | 5.5 | 5.5 | 5.5 |
| Antioxidant (6) | 1.5 | 1.5 | 1.5 | 1.5 |
| Antioxidant (7) | 1 | 1 | 1 | 1 |
| Antiozone wax | 1 | 1 | 1 | 1 |
| ZnO | 2.7 | 2.7 | 2.7 | 2.7 |
| Stearic acid | 2.5 | 2.5 | 2.5 | 2.5 |
| Sulphenamide (8) | 1.8 | 1.8 | 1.8 | 1.8 |
| Sulphur | 1.5 | 1.5 | 1.5 | 1.5 |

(1) SBR: SBR with 25% of styrene units and 56% of 1,2-units of the butadiene part
(2) IR: Natsyn 2200 polyisoprene
(3) 1,3-dipolar compound, the synthesis of which is described above in section II.2
(4) silica: Zeosil 1165 MP from Rhodia (HDS type)
(5) TESPT (Si69 from Degussa)
(6) 2,2,4-trimethyl-1,2-dihydroquinoline
(7) N-(1,3-dimethylbutyl)-N'-phenyl-p-phenylenediamine from Flexsys
(8) N-cyclohexyl-2-benzothiazolesulphenamide (Santocure CBS from Flexsys)

The results are recorded in Table (II) below.

TABLE (II)

| Properties in the | Composition | | | |
|---|---|---|---|---|
| cured state | A | B | C | D |
| ASM100 at 23° C. | 2.83 | 3.47 | 2.31 | 2.61 |
| tan(δ)max at 23° C. | 0.28 | 0.19 | 0.21 | 0.05 |
| ΔG* at 23° C. | 4 | 0.23 | 5.36 | 0.35 |
| G* at 100° C. | 1.61 | 1.78 | 1.59 | 1.50 |
| tan(δ)max at 100° C. | 0.13 | 0.08 | 0.12 | 0.05 |

The compositions B and D exhibit, at 23° C., a modulus ASM100 at 23° C. which is much greater than that of the respective control compositions A and C. This increase in stiffness in the cured state is obtained although a very significant decrease in the hysteresis at 23° C. is also observed for B and D, in comparison with their respective controls A and C. The increase in the stiffness in the cured state is all the more remarkable as the fall in hysteresis is very strong, since the value of tan(δ)max at 23° C. decreases by 32% for the SBR matrix and by 76% for the IR matrix and that of ΔG* at 23° C. decreases by 94% for the SBR matrix and by 93% for the IR matrix.

As good road behaviour of a tyre is generally associated with a high stiffness in the cured state of the composition which constitutes its tread, this result foretells good road behaviour of a tyre having a tread comprising a composition B or D.

Furthermore, it is observed that, in comparison with their respective controls, the compositions according to the invention B and D retain a comparable level of stiffness in the cured state at 100° C., indeed even better for the composition B. These results presage a temperature versatility of the rubber composition in accordance with the invention. This is because it may be expected that a tread containing the composition B or D will make it possible for the tyre to have a road behaviour at least just as good as would be had by the control composition A or C, during more extreme rolling conditions, in particular for sports car tyres rolling at high speed.

II.4-2 Example 2

The formulations (in phr) of the compositions E and F are described in Table (III). The compositions E and F, based on polyisoprene (IR) and silica, differ in that the composition F contains the 1,3-dipolar compound, the synthesis of which is described in section II.3. The compositions C and D, based on polyisoprene and silica, differ in that the composition D contains the 1,3-dipolar compound.

TABLE III

| | Composition | |
|---|---|---|
| | E not in accordance | F in accordance |
| IR (1) | 100 | 100 |
| 1,3-Dipolar compound (2) | — | 1.16 |
| Carbon black N234 | 3 | 3 |
| Silica (3) | 55 | 55 |
| Silane (4) | 5.5 | 5.5 |
| Antioxidant (5) | 1 | 1 |
| Antioxidant (6) | 1.5 | 1.5 |
| Antiozone wax | 1 | 1 |
| ZnO | 2.7 | 2.7 |
| Stearic acid | 2.5 | 2.5 |
| Sulphenamide (7) | 1.8 | 1.8 |
| Sulphur | 1.5 | 1.5 |

(1) IR: polyisoprene containing 98% by weight of cis-1,4-units
(2) 1,3-dipolar compound, the synthesis of which is described above in section II.3
(3) silica: Zeosil 1165 MP from Rhodia (HDS type)
(4) TESPT (Si69 from Degussa)
(5) 2,2,4-trimethyl-1,2-dihydroquinoline
(6) N-(1,3-dimethylbutyl)-N'-phenyl-p-phenylenediamine from Flexsys
(7) N-cyclohexyl-2-benzothiazolesulphenamide (Santocure CBS from Flexsys)

The results are recorded in Table (IV) below.

TABLE (IV)

| Properties in the | Composition | |
|---|---|---|
| cured state | E | F |
| ASM100 at 23° C. | 1.84 | 2.55 |
| tan(δ)max at 23° C. | 0.23 | 0.07 |
| ΔG* at 23° C. | 3.27 | 0.35 |
| G* at 100° C. | 1.35 | 1.25 |
| tan(δ)max at 100° C. | 0.13 | 0.05 |

The composition F exhibits, at 23° C., a modulus ASM100 at 23° C. which is much greater than that of the control composition E. This increase in stiffness in the cured state is obtained although a very significant decrease in the hysteresis at 23° C. is also observed for F, in comparison with the control E. The increase in the stiffness in the cured state is all the more remarkable as the fall in hysteresis is very strong.

II.4-3 Example 3

The formulations (in phr) of the compositions G, CG, H and CH are described in Table V. The compositions G and H differ from their respective control compositions CG and CH in that they contain the 1,3-dipolar compound, the synthesis of which is described in section II.2. The silanes are introduced into the composition at the same molar content of silicon: as the silane disulphide does not release sulphur, in contrast to the silane TESPT, the content of soluble sulphur has been increased by 80% in the compositions H and CH in order to have the same content of sulphur as the other compositions G and CG.

TABLE (V)

| | Composition | | | |
|---|---|---|---|---|
| | CG not in accordance | G in accordance | CH not in accordance | H in accordance |
| SBR (1) | 100 | 100 | 100 | 100 |
| Carbon black (2) | 4 | 4 | 4 | 4 |
| Silica (3) | 84 | 84 | 84 | 84 |
| Silane (4) | 6.7 | 6.7 | — | — |
| Silane (5) | — | — | 5.93 | 5.93 |
| 1,3-Dipolar compound (6) | — | 1.88 | — | 1.88 |
| Antioxidant (7) | 1.9 | 1.9 | 1.9 | 1.9 |
| Oil (8) | 4.8 | 4.8 | 4.8 | 4.8 |
| Antiozone wax | 1.5 | 1.5 | 1.5 | 1.5 |
| Resin (9) | 20 | 20 | 20 | 20 |
| ZnO | 2.5 | 2.5 | 2.5 | 2.5 |
| Stearic acid | 2.5 | 2.5 | 2.5 | 2.5 |
| Sulphur | 1.2 | 1.2 | 2.2 | 2.2 |
| Sulphenamide (10) | 1.9 | 1.9 | 1.9 | 1.9 |

(1) SBR: SBR with 26% of styrene units and 25% of 1,2-units of the butadiene part
(2) N234
(3) silica: Zeosil 1165 MP from Rhodia (HDS type)
(4) TESPT (Si69 from Degussa)
(5) Si 75 ® from Evonik
(6) 1,3-dipolar compound, the synthesis of which is described above in section II.2
(7) N-(1,3-dimethylbutyl)-N'-phenyl-p-phenylenediamine from Flexsys
(8) MES oil (Catenex SNR from Shell)
(9) $C_5/C_9$ resin: ECR-373 from Exxon
(10) N-cyclohexyl-2-benzothiazolesulphenamide (Santocure CBS from Flexsys)

The results are recorded in Table (VI) below.

TABLE (VI)

| | Composition | | | |
|---|---|---|---|---|
| Properties in the cured state | CG not in accordance | G in accordance | CH not in accordance | H in accordance |
| ASM100 at 23° C. | 2.81 | 3.99 | 3.21 | 4.44 |
| ASM300 at 23° C. | 3.15 | 5.05 | 3.69 | 4.99 |
| tan(δ)max at 23° C. | 0.27 | 0.17 | 0.25 | 0.16 |
| ΔG* at 23° C. | 7.14 | 1.59 | 9.11 | 1.7 |
| G* at 100° C. | 1.73 | 1.87 | 2.09 | 1.99 |
| tan(δ)max at 100° C. | 0.22 | 0.12 | 0.21 | 0.12 |

The compositions in accordance with the invention exhibit a stiffness hysteresis compromise which is greatly improved in comparison with their respective controls.

The invention claimed is:

1. A rubber composition based on:
   at least one diene elastomer;
   a reinforcing filler; and
   a 1,3-dipolar compound of formula (I):

Q-A-B       (I)

wherein Q comprises a dipole containing at least one nitrogen atom,
   wherein A is an atom or a group of atoms connecting Q to B, wherein B comprises a ring of formula (II):

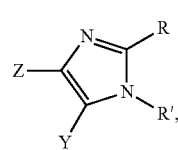

(II)

and
   wherein three of the four symbols Z, Y, R and R', which are identical or different, each represent an atom or a group of atoms, it being possible for Z and Y to form, together with the carbon atoms to which they are attached, a ring, and the fourth symbol Z, Y, R or R' denotes a direct attachment to A.

2. The rubber composition according to claim 1, wherein R' denotes a direct attachment to A.

3. The rubber composition according to claim 2, wherein Z and Y are each a hydrogen atom.

4. The rubber composition according to claim 2, wherein Z and Y form, together with the carbon atoms to which they are attached, a ring.

5. The rubber composition according to claim 1, wherein R represents a hydrogen atom or a carbon-based group which can contain at least one heteroatom.

6. The rubber composition according to claim 5, wherein R is an alkyl group that contains from 1 to 12 carbon atoms.

7. The rubber composition according to claim 1, wherein A is an aliphatic group or an aromatic group.

8. The rubber composition according to claim 7, wherein A is an alkylene group containing from 1 to 20 carbon atoms or an arylene group.

9. The rubber composition according to claim 1, wherein the 1,3-dipolar compound is selected from the group consisting of nitrile oxides, nitrile imines and nitrones.

10. The rubber composition according to claim 9, wherein Q contains a —C≡N→O unit.

11. The rubber composition according to claim 10, wherein Q comprises a unit of formula (III):

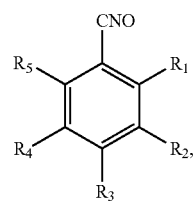

(III)

wherein four of the five symbols $R_1$ to $R_5$, which are identical or different, are each an atom or a group of atoms, and the fifth symbol denotes a direct attachment to A, and
   wherein $R_1$ and $R_5$ are not H.

12. The rubber composition according to claim 11, wherein $R_1$, $R_3$ and $R_5$ are each an alkyl group of 1 to 6 carbon atoms.

13. The rubber composition according to claim 12, wherein the 1,3-dipolar compound is 2,4,6-trimethyl-3-((2-methyl-1H-imidazol-1-yl)methyl)benzonitrile oxide or 2,4,6-triethyl-3-((2-methyl-1H-imidazol-1-yl)methyl)benzonitrile oxide.

14. The rubber composition according to claim 9, wherein Q contains a —C=N(→O)— unit.

15. The rubber composition according to claim 14, wherein Q comprises a unit of formula (IV) or (V):

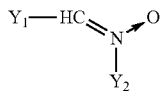
(IV)

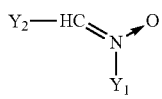
(V)

wherein $Y_1$ is an aliphatic group or an aromatic group containing from 6 to 20 carbon atoms, and wherein $Y_2$, comprising a direct attachment to A, is an aliphatic group or an aromatic group comprising, on its benzene nucleus, the direct attachment to A.

16. The rubber composition according to claim 15, wherein the 1,3-dipolar compound is of formula (IVa), (IVb), (Va) or (Vb):

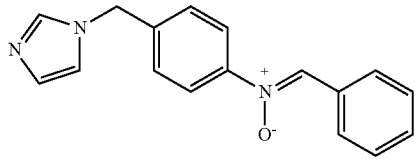
(IVa)

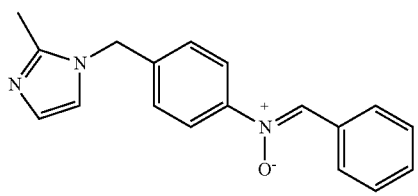
(IVb)

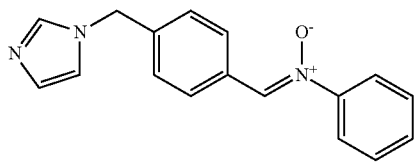
(Va)

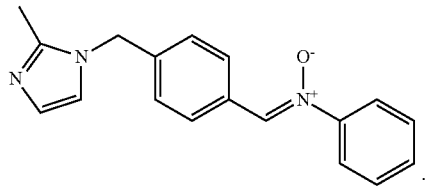
(Vb)

17. The rubber composition according to claim 1, wherein an amount of 1,3-dipolar compound is between 0 and 3 molar equivalents of imidazole ring per 100 moles of monomer units constituting the diene elastomer.

18. The rubber composition according to claim 1, wherein the diene elastomer is an essentially unsaturated elastomer selected from the group consisting of polybutadienes, polyisoprenes, butadiene copolymers, isoprene copolymers and mixtures thereof.

19. The rubber composition according to claim 1, wherein the reinforcing filler comprises an organic filler.

20. The rubber composition according to claim 1, wherein the reinforcing filler comprises a reinforcing inorganic filler.

21. The rubber composition according to claim 20, wherein the reinforcing inorganic filler is a silica.

22. The rubber composition according to claim 20, wherein the rubber composition further comprises a silane coupling agent for bonding the reinforcing inorganic filler to the diene elastomer.

23. The rubber composition according to claim 1, wherein the rubber composition further comprises a crosslinking system.

24. A tread which comprises a rubber composition according to claim 1.

25. A tire comprising a rubber composition according to claim 1.

26. A process for preparing a rubber composition according to claim 23, said process comprising the steps of:
adding, during a first non-productive stage, to the diene elastomer, the 1,3-dipolar compound, the reinforcing filler and, if appropriate, a coupling agent, by kneading thermomechanically until a maximum temperature of between 130° C. and 200° C. is reached;
cooling the combined mixture to a temperature of less than 100° C.;
subsequently incorporating the crosslinking system; and kneading up to a maximum temperature of less than 120° C.

* * * * *